United States Patent
Uchida

(10) Patent No.: US 8,414,122 B2
(45) Date of Patent: Apr. 9, 2013

(54) MEDICAL IMAGING APPARATUS

(75) Inventor: Hiroki Uchida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 605 days.

(21) Appl. No.: 12/491,141

(22) Filed: Jun. 24, 2009

(65) Prior Publication Data

US 2009/0323022 A1 Dec. 31, 2009

(30) Foreign Application Priority Data

Jun. 26, 2008 (JP) .................................. 2008-167061

(51) Int. Cl.
*A61B 3/14* (2006.01)
*A61B 3/00* (2006.01)
(52) U.S. Cl. ...................................... 351/206; 351/246
(58) Field of Classification Search .................. 351/206, 351/246
See application file for complete search history.

(56) References Cited

U.S. PATENT DOCUMENTS

2006/0139944 A1* 6/2006 Van Saarloos et al. ....... 362/572
2006/0280489 A1 12/2006 Mizuochi

FOREIGN PATENT DOCUMENTS

| JP | 9248279 A | 9/1997 |
| JP | 2004141291 A | 5/2004 |
| JP | 2006-115925 A | 5/2006 |
| JP | 2006-345955 A | 12/2006 |

OTHER PUBLICATIONS

English translation of JP2006115925.

* cited by examiner

*Primary Examiner* — Jack Dinh
(74) *Attorney, Agent, or Firm* — Canon U.S.A., Inc. IP Division

(57) ABSTRACT

A medical imaging apparatus includes an imaging unit configured to capture an image of a subject, an imaging sequence registration unit configured to register an imaging sequence, and a display unit configured to display the imaging sequence registered by the imaging sequence registration unit.

20 Claims, 19 Drawing Sheets

FIG. 3

IMAGING SEQUENCE DISPLAY PAGE — 23

| No. | IMAGING MODE | RIGHT/LEFT EYE | IMAGING TIMING | PERMISSIBLE TIME |
|---|---|---|---|---|
| 1 | Color | RIGHT EYE | — | — |
| 2 | Color | LEFT EYE | — | — |
| | | | | |
| | | | | |
| | | | | |
| | | | | |

FIG. 4

IMAGING SEQUENCE REGISTRATION PAGE — 24

IMAGING MODE: ○ Color ● Fluo

RIGHT/LEFT EYE: ○ LEFT EYE ○ RIGHT EYE ● UNSPECIFIED

IMAGING TIMING: ○ UNSPECIFIED
● SPECIFIED [ 5'00" ] — 25

PERMISSIBLE TIME: ● AUTOMATIC REGISTRATION
○ SPECIFIED [ ]

[ REGISTER ] — 26

FIG. 6

IMAGING SEQUENCE DISPLAY PAGE ~27

| No. | IMAGING MODE | RIGHT/LEFT EYE | IMAGING TIMING | PERMISSIBLE TIME |
|---|---|---|---|---|
| 1 | Fluo | — | 0'04" | ±0'01" |
| 2 | Fluo | — | 0'05" | ±0'01" |
| 3 | Fluo | — | 0'10" | ±0'02" |
| 4 | Fluo | — | 0'30" | ±0'07" |
| 5 | Fluo | — | 1'10" | ±0'15" |
| 6 | Fluo | — | 2'00" | ±0'30" |
| 7 | Fluo | — | 5'00" | ±1'15" |

MEDICAL IMAGING APPARATUS

BACKGROUND OF THE INVENTION

1. Field of the Invention

The present invention relates to a medical imaging apparatus, such as a fundus camera, to be used for a group examination, at an ophthalmologist's office, and the like.

2. Description of the Related Art

Hitherto, fundus imaging using a fundus camera has been widely used for screening by a group examination, and a diagnosis of an ophthalmological disease. In recent years, a method for recording a fundus image as digital data has been widely used. Imaged data is recorded in portable type recording media or built-in hard disk drives in personal computers (PCs).

The fundus imaging using a fundus camera is known in that a large number of images are taken in a short time. More particularly, in a group examination for screening, a large number of subjects should be taken. Thus, sometimes, a health examination on that day may be terminated due to an operator's carelessness without photographing a part of subjects.

When omission of photographing of subjects occurs in a group examination, it is necessary to request the subjects to come to a health examination site or a health examination facility again. When omission of photographing of subjects occurs in an ophthalmologist's office, it is necessary to apply mydriatics or to intravenously administer fluorescence agents to the subjects. However, a reexamination may be a large physical and mental burden.

Accordingly, Japanese Patent Application Laid-Open No. 2006-115925 discusses an ophthalmologic imaging apparatus that can detect, at a stage of completion of a health examination on that day, omission of photographing of a subject by comparing a list of predetermined subjects to be captured and that of captured subjects.

However, it is insufficient that subjects to be captured have been imaged only without omission of photographing of a subject. That is, it is important not only whether subjects are imaged, but which contents of fundus are imaged. An appropriate diagnosis is made by a physician on each captured fundus image. However, in order to make this appropriate diagnosis, it is necessary to take an appropriate number of images of an appropriate part of each subject at an appropriate timing according to a diagnosis object.

For example, fundus imaging in a group examination aims mainly at screening of diabetes, glaucoma, and the like. In the fundus imaging aiming at the screening, it is necessary to image both of left and right eyes of each subject, because it is impossible to know which of the right and left eyes of each subject is diseased. Accordingly, in group examinations, it is often obligated to take one image for each of the right and left eyes of each subject without fail.

However, a conventional fundus imaging apparatus has no means for transmitting, to operators, information indicating which of the right and left eyes of each subject is captured, and how many images of the eye is captured. Therefore, the conventional fundus imaging apparatus has a problem in that no operators know which of the right and left eyes of each subject is captured, and how many images of the eye is captured.

On the other hand, in fundus imaging in an ophthalmologist's office, sometimes, in order to make a diagnosis on a diseased part in more detail, fluorescence photographing is performed by intravenously administering a fluorescence agent to a subject, in addition to color imaging of a fundus. In this fluorescence photographing, it is extremely important for making a diagnosis to image a fundus at a timing at which the fluorescence agent reaches the diseased part. Thus, in an ophthalmologist's office, a photographing timing and the number of images of a fundus to be taken at each fluorescence photographing are determined in advance.

However, the conventional fundus image-taking apparatus has no means for informing operators of information indicating the imaging timing and the number of images of a fundus at each fluorescence photographing. Accordingly, the conventional fundus imaging apparatus has a problem in that operators cannot know the imaging timing in which certain seconds have elapsed since a fluorescence agent is intravenously administered to a subject, and how many images of a fundus of the subject's eye should be imaged at the timing.

Thus, when the conventional fundus imaging apparatus is used, an operator does not know how to take the fundus image. Consequently, sometimes, operators forget to take fundus images needed for a diagnosis of a disease.

SUMMARY OF THE INVENTION

The present invention is directed to a medical imaging apparatus that enables an imaging apparatus operator to easily know how fundus imaging should be performed at an appropriate imaging timing.

According to an aspect of the present invention, a medical imaging apparatus includes an imaging unit configured to capture an image of a subject, an imaging sequence registration unit configured to register an imaging sequence, and a display unit configured to display the imaging sequence registered by the imaging sequence registration unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 illustrates an imaging sequence display screen in the color imaging mode.

FIG. 4 illustrates an imaging sequence registration screen in fluorescence imaging mode.

FIG. 6 illustrates a imaging sequence display screen in the fluorescence imaging mode.

DETAILED DESCRIPTION OF THE EMBODIMENTS

Various exemplary embodiments, features, and aspects of the invention will be described in detail below with reference to the drawings.

Figure 1:
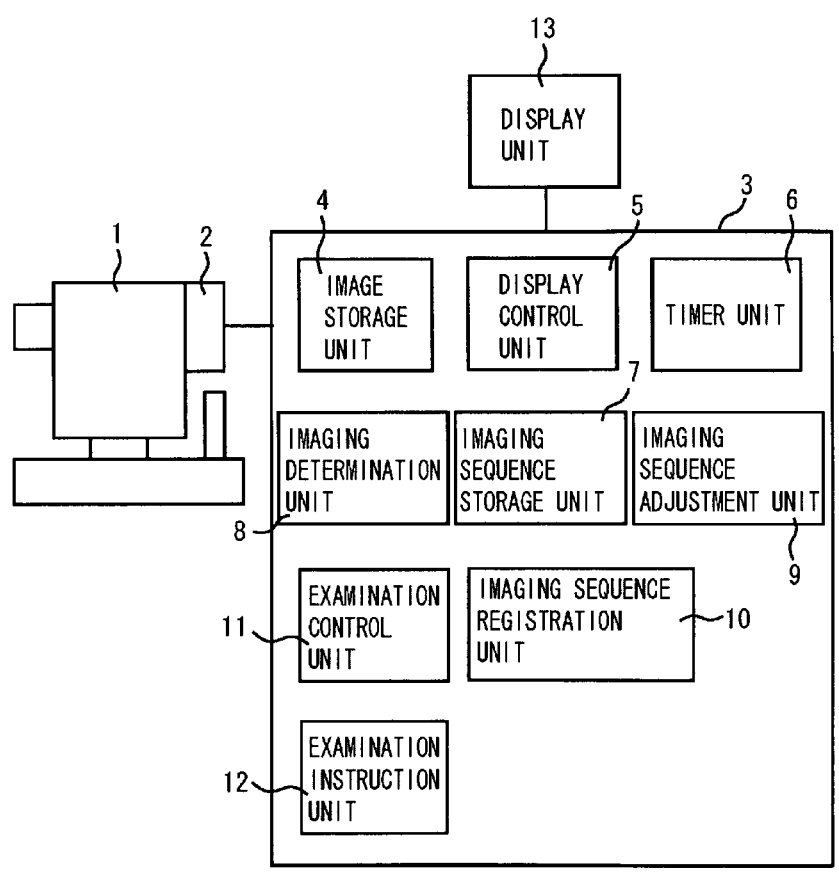
FIG. 1 illustrates a configuration of a fundus imaging apparatus.

FIG. 1 illustrates a configuration of a fundus imaging apparatus according to the present embodiment, which serves as a medical imaging apparatus.

A digital camera 2 that is provided with an image sensor that captures an image of a fundus of a subject's eye is attached to a fundus camera 1. An image captured by the digital camera 2 is output to an information processing apparatus 3.

The information processing apparatus 3 includes an image storage unit 4, a display control unit 5, a timer unit 6, an imaging sequence storage unit 7, an imaging determination unit 8, an imaging sequence adjustment unit 9, an imaging sequence registration unit 10, an examination control unit 11, and an examination instruction unit 12. A display unit 13 is connected to the information processing unit 3.

The display control unit 5 controls a display operation of the display unit 13, based on images stored in the image storage unit 4, imaging sequences stored in the imaging sequence storage unit 7, and a time measured by the timer unit 6. The "imaging sequence" is defined as an imaging procedure including at least one of an imaging mode, information representing which of right/left eyes is a target to be captured, an imaging timing, and a permissible time of an imaging timing.

The imaging determination unit 8 determines whether imaging is performed based on the imaging procedure stored in the imaging sequence storage unit 7. The imaging sequence adjustment unit 9 can adjust an imaging sequence. The examination instruction unit 12 instructs the examination control unit 11 to end an examination. The examination instruction unit 12 can control end of an examination, based on determination made by the imaging determination unit 8.

When fundus imaging is performed, an imaging procedure suitable for a diagnosis is registered as an imaging sequence. Contents of the registered imaging sequence change according to a purpose of a diagnosis. Thus, an example of color imaging in a group examination and that of fluorescence imaging in an ophthalmologist's office are described below.

Figure 2:
FIG. 2 illustrates an imaging sequence registration screen in a color imaging mode.

FIG. 2 illustrates an imaging sequence registration screen 21 in a group examination, which is displayed on a display screen of the display unit 13. An administrator of the group examination registers an imaging sequence via the imaging sequence registration unit 10 and stores the registered sequence in the imaging sequence storage unit 7 before the group examination.

On this screen, conditions for each single fundus image are input. In the registration for each imaging sequence, first, an imaging mode is selected. Because color imaging using a non-mydriatic type fundus camera is performed, an option "Color" is selected. Because the group examination aims at screening, fluorescence imaging is not performed.

Next, right/left eyes are designated. A diseased part cannot be specified in the color imaging that aims at screening of the disease. It is necessary to capture images of fundi of both right and left eyes of each subject. Thus, both the imaging sequences respectively corresponding to the right and left eyes of each subject are registered. On the imaging sequence registration screen illustrated in FIG. 2, information representing the selection of the "right eye" is input.

On the other hand, in the color imaging, no fluorescence agent is used. Thus, the same fundus image can be captured, regardless of the imaging timing. Consequently, options "unspecified" and "automatic registration" are respectively selected for input fields corresponding to an imaging-timing setting means and a permissible-time setting means on this registration screen.

Finally, when selection of a registration button 22 provided on a lower part of the registration screen is detected, an input imaging sequence is added to the imaging sequence storage unit 7. Similarly, when an imaging sequence for the color imaging of the "left eye" is added thereto, a total of two imaging sequences respectively corresponding to the right and left eyes are set, as illustrated in FIG. 3.

FIG. 4 illustrates an imaging sequence registration screen 24 in the case of fluorescence imaging performed in an ophthalmologist's office. When fluorescence imaging is performed, imaging sequences are registered before an examination, similarly to the color imaging. On the imaging sequence registration screen 24, an imaging timing and the like for each single image of a fundus are input.

First, an imaging mode is selected. In the ophthalmologist's office, fluorescence imaging using a mydriatic type fundus camera is performed. Thus, an option "Fluo" is selected as the imaging mode on the imaging sequence registration screen 24.

Next, the right eye or the left eye is designated. When fluorescence imaging is performed, in many cases, a diseased part has already been specified. Thus, the right eye or the left eye is designated. However, as illustrated in FIG. 4, the option "unspecified" can be selected by designating neither the right eye nor the left eye.

Next, an imaging timing is designated. When fluorescence imaging is performed, a time having elapsed after the intravenous administration of a fluorescence agent is an important factor. Thus, it is necessary to preliminarily designate a timing at which imaging is performed.

Thus, the time having elapsed since the intravenous administration of a fluorescence agent is registered in the imaging timing input field 25. However, the imaging timing is not limited to the time having elapsed since the administration of the fluorescence agent. The imaging timing may be set to be a time having elapsed since the start of the examination. Alternatively, the imaging timing can be set to be a time having elapsed since a first image is captured.

Next, a permissible time is registered. Intrinsically, fluorescence imaging should be performed at a set imaging timing. However, because an operator manually performs imaging, it is inevitable that the imaging timing is slightly deviated.

It is possible due to a blink of a subject or to insufficient ocular fixation thereof that the registered imaging timing has passed. Thus, a permissible time corresponding to the imaging timing can be registered in consideration of the above-described deviation.

Figure 5:
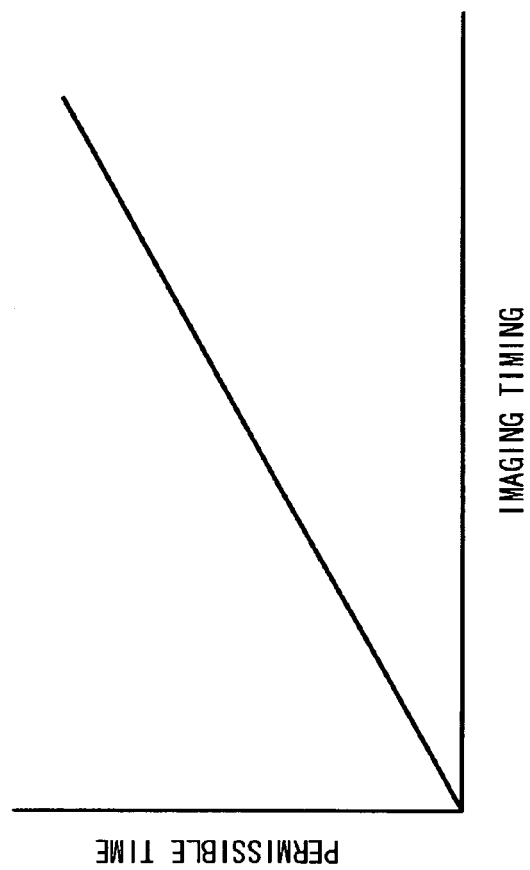
FIG. 5 illustrates a relationship between a permissible time and an imaging timing.

According to the present embodiment, an option "automatic registration", in which the permissible time is registered automatically, is selected. When the "automatic registration" of the permissible time is selected, the permissible time is automatically set to increase in proportion to the elapsed time set as an imaging timing, as illustrated in FIG. 5.

Generally, the older the subject becomes, the more the ocular fixation stability of the subject increases. Thus, the permissible time can be automatically registered so as to change according to the subject's age. When color imaging is performed, the tolerance of the permissible time for the imaging timing is larger, as compared with that of fluorescence imaging. Therefore, the permissible time can be automatically registered so as to vary according to an imaging mode. Alternatively, the apparatus may be configured so that the permissible time is manually set to an optional value.

Then, when the selection of the registration button 26 provided on the screen is finally detected, the input imaging sequence is stored in the imaging sequence storage unit 7. This operation of registering the imaging sequence is repeated. Thus, when a series of the fluorescence imaging sequences is added thereto, the imaging sequences are registered therein in the order of the imaging timing, as indicated on the imaging sequence display screen illustrated in FIG. 6.

Although the example of manually setting the imaging sequence has been described above, the imaging sequence may be set via a network or the like.

Figure 7:
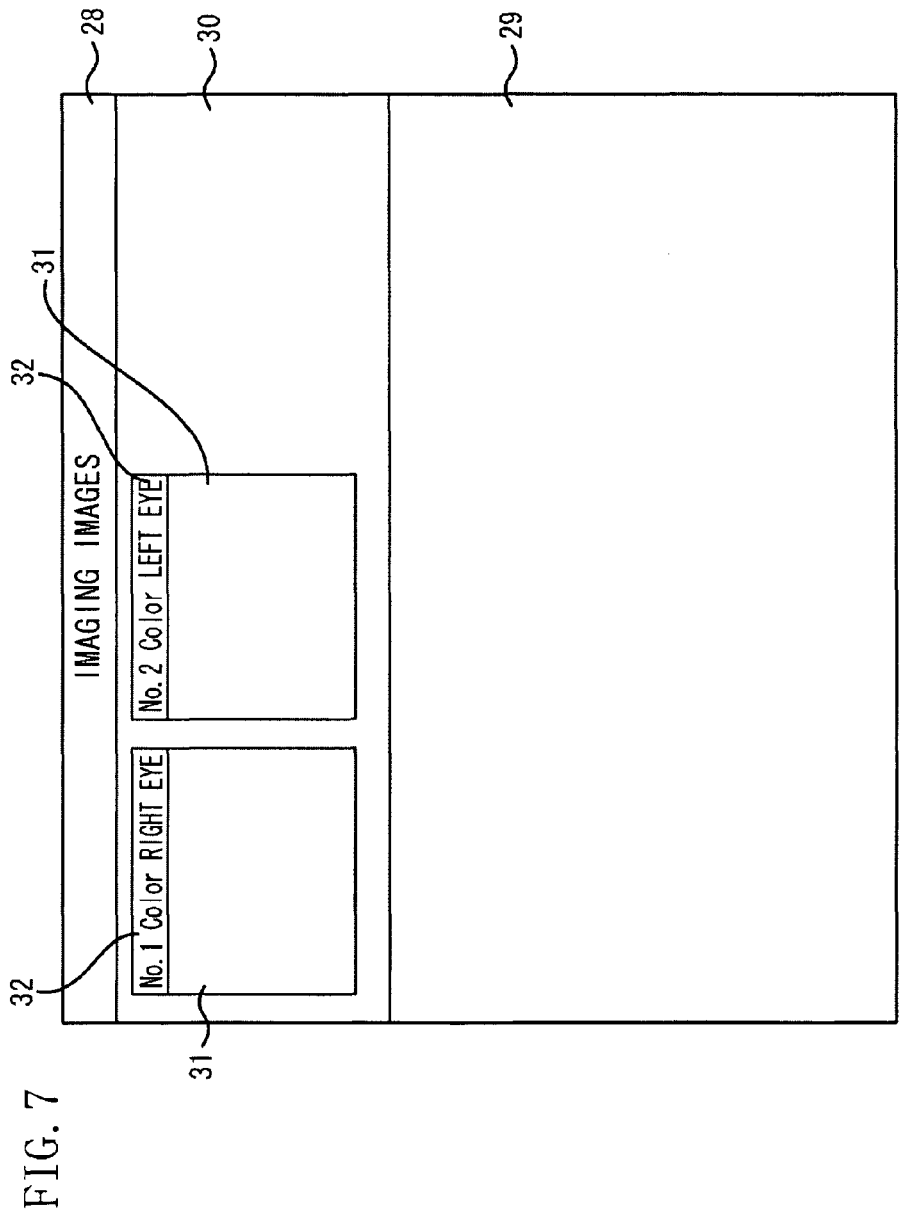
FIG. 7 illustrates an imaging screen before imaging is performed in the color imaging mode.

When color imaging is performed in a group examination, an operator operates, before imaging is performed, the examination instruction unit 12 to thereby cause the display 13 to display the imaging screen 28 illustrated in FIG. 7. On this imaging screen 28, a main display region 29 and a thumbnail display portion 30 are arranged. In the thumbnail display portion 30, image frames 31 corresponding to imaging sequences stored in the imaging sequence storage unit 7 are displayed. Photographing conditions registered in each imaging sequence are displayed in an imaging condition field 32.

Assuming that a total of two imaging sequences respectively corresponding to the right and left eye imaging are registered to perform color imaging, as illustrated in FIG. 3, internal portions of two image frames 31 and the two imaging condition fields 32 are displayed. Additionally, no images are displayed in the image frames 31 until imaging is actually performed.

Figure 8:
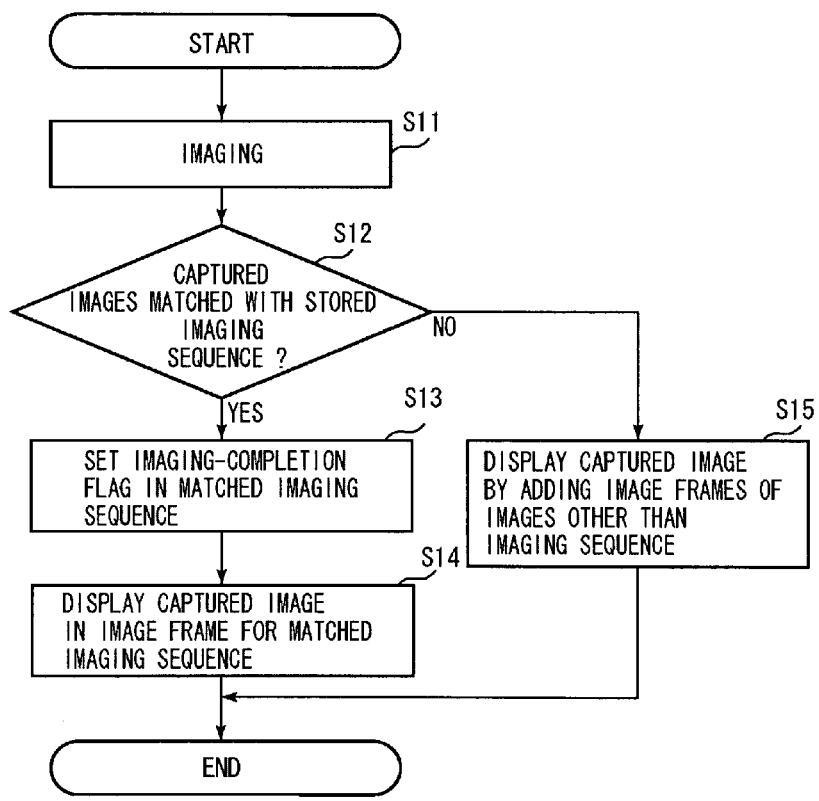
FIG. 8 is a flowchart illustrating an imaging operation performed in the color imaging mode.

FIG. 8 is a flowchart illustrating an imaging procedure in the color imaging mode. First, in step S11, the display control unit 5 causes the display unit 13 to display the imaging screen 28 illustrated in FIG. 7. Then, the digital camera 2 performs imaging of the fundus of the subject's eye in response to an operation of pressing an imaging switch provided in the fundus camera (not illustrated).

The captured fundus image is stored in the image storage unit 4 of the information processing apparatus 3 as image data after photo-electrically converted by the digital camera 2. In addition, information representing the designated eye (right or left) and the imaging mode is stored in the image storage unit 4 together with the image data captured by the digital camera 2.

In step S12, when the imaging determination unit 8 detects that image data is stored in the image storage unit 4, a comparison process is performed for comparing the image data with each imaging sequence stored in the imaging sequence storage unit 7 and determining whether the image data is matched with each imaging sequence stored in the storage unit 7. This comparison process is performed according to a flowchart illustrated in FIG. 10, which will be described below.

In step S12, if such information is matched with each other (YES in step S12), the imaging determination unit 8 determines that imaging has been performed based on the imaging sequence. Then, the process proceeds to step S13 in which the determination unit 8 sets an imaging-completion flag in the matched imaging sequence. Subsequently, the process proceeds to step S14.

Figure 9:
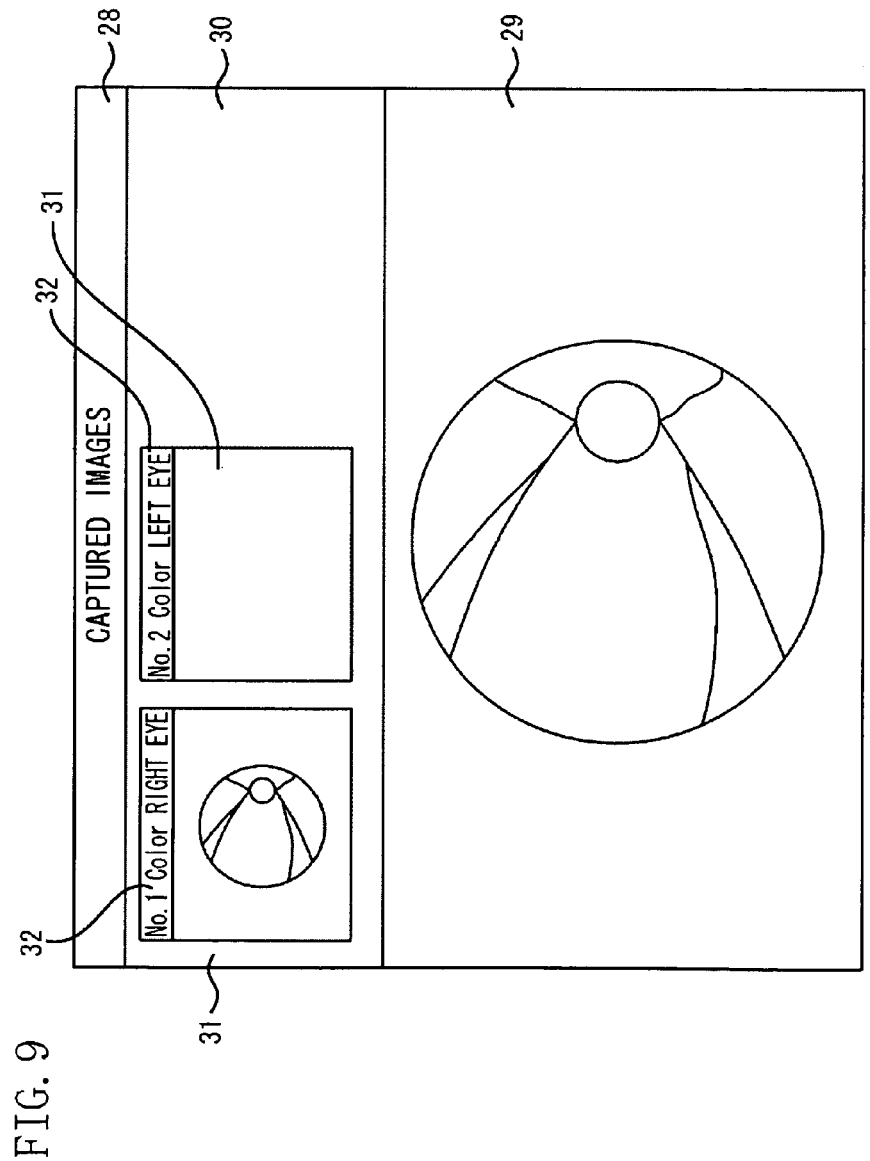
FIG. 9 illustrates an imaging screen after imaging is performed in the color imaging mode.

In step S14, when the image data stored in the image storage unit 4 is an image obtained by imaging, e.g., the right eye, the display control unit 5 causes the display unit 13 to display a captured image in the main display region 29, as illustrated in FIG. 9. In addition, the display control unit 5 causes the display unit 13 to display a captured image in the image frame 31 corresponding to an associated imaging sequence that satisfies the condition. Consequently, the operator can recognize the image frame 31 in which the captured image is embedded. Thus, the operator can easily grasp that the imaging sequence is performed.

On the other hand, in step S12, if no registered imaging sequence satisfies the condition (NO in step S12), the imaging determination unit 8 determines that imaging of an image captured according to the conditions other than those registered in the imaging sequences is performed. Then, the process proceeds to step S15 in which the display control unit 5 causes the display unit 13 to display a captured image in the main display region 29 and to create a new image frame in the thumbnail display portion 30 and display the captured image in this image frame.

Figure 10:
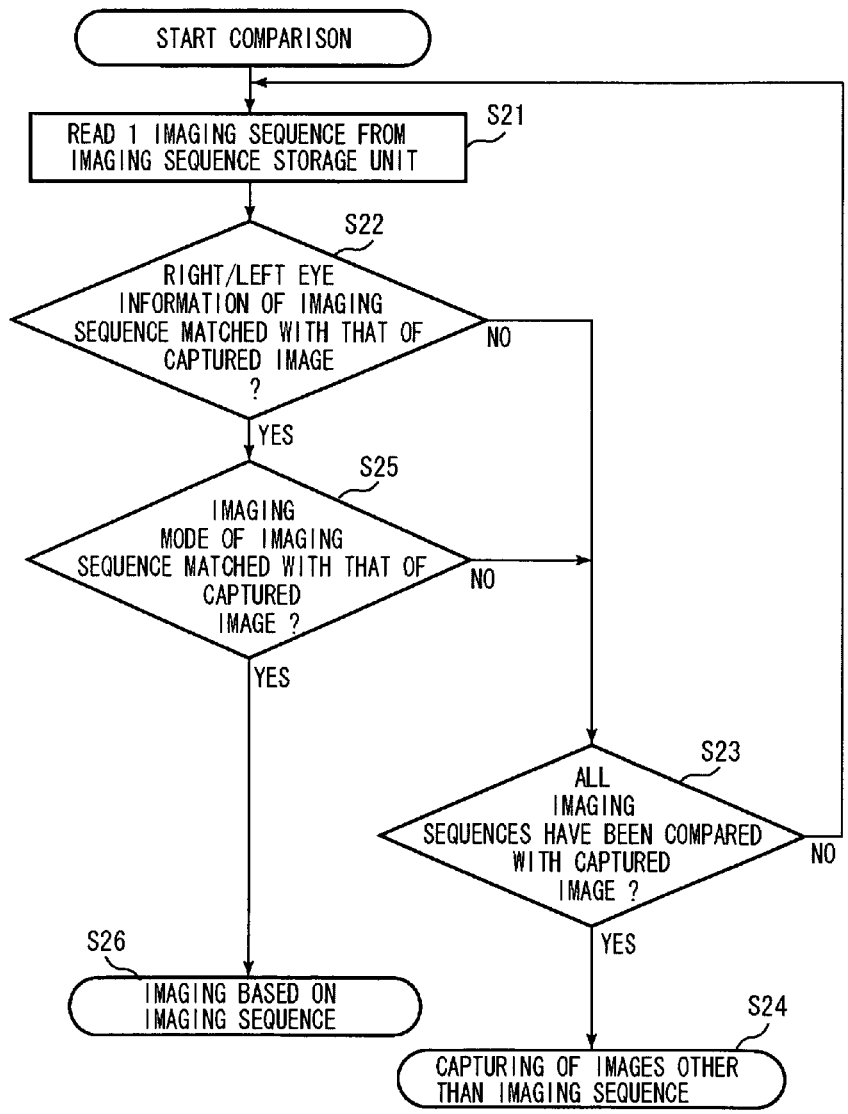
FIG. 10 is a flowchart illustrating a comparison process performed in the color imaging mode.

FIG. 10 is a flowchart illustrating the comparison process to be performed in step S12 illustrated in FIG. 8.

First, in step S21, the imaging determination unit 8 reads the first registered imaging sequence from the imaging sequence storage unit 7. Next, in step S22, the imaging determination unit 8 compares the information designating the right or left eye stored together with the imaged data in the image storage unit 4, with that designated in the imaging sequence to determine whether the information designating the right or left eye stored in the image storage unit 4 with that designating the right or left eye designated in the imaging sequence.

If the information designating the right or left eye stored in the image storage unit 4 is not matched with that designated in the imaging sequence (NO in step S22), the process proceeds to step S23 in which the imaging determination unit 8 determines whether the registered imaging sequence to be compared is the last one that has been registered.

If the imaging determination unit 8 determines that the registered imaging sequence to be compared is the last one (YES in step S23), the imaging determination unit 8 determines that the comparison with all of the imaging sequences is finished. Then, the process proceeds to step S24 in which the imaging determination unit 8 determines that the image data stored in the image storage unit 4 is an image captured according to the conditions other than those registered in the imaging sequences. If the imaging determination unit 8 determines that the imaging sequence is not the last one (NO in step S23), the process returns to step S21, because the next registered imaging sequence is present. Subsequently, similar steps are repeated.

In step S22, if the information representing the right or left eye is matched with that registered in the imaging sequence (YES in step S22), the process proceeds to step S25, in which the imaging determination unit 8 determines whether the information representing the imaging mode stored in the image storage unit 4 is matched with that of the imaging mode registered in the imaging sequence.

If the information representing the imaging mode stored in the storage unit 4 is not matched with that of the imaging mode registered in the imaging sequence (NO in step S25), the process proceeds to step S23. If the information representing the imaging mode stored in the storage unit 4 is matched with that representing the imaging mode registered in the imaging sequence (YES in step S25), the process proceeds to step S26, in which the imaging determination unit 8 determines that the imaging is performed based on the conditions registered in the imaging sequence.

Next, in the imaging procedure of the fluorescence imaging performed in an ophthalmologist's office, an operator operates the examination instruction unit 12 (not illustrated) before the imaging is performed. Thus, the display unit 13 is caused to display an imaging screen 41 illustrated in FIG. 11. The imaging screen 41 includes a main display region 42, a thumbnail display portion 43, and a time-line display portion 44 serving as a time axis.

On the thumbnail portion 43, an image frame 45 corresponding to each imaging sequence stored in the imaging sequence storage unit 7 is displayed. The imaging conditions registered in each imaging sequence stored in the imaging sequence storage unit 7 are displayed in the imaging condition field 46.

The time line display portion 44 is marked with scale marks at uniform intervals corresponding to each unit time. In the time line display portion 44, a time having elapsed since the administration of a fluorescence agent is displayed. The image frame 45 and the imaging condition field 46 are displayed at positions above the time line displayed in the time line display portion 44, which correspond to each of the imaging timing registered in each imaging sequence.

An imaging timing line 47 indicating the imaging timing registered in each imaging sequence, and a permissible time display region 48 indicating a permissible time length for each imaging timing are provided on the time line display portion 44.

In addition, an elapsed time display line 49 representing a time having elapsed since the intravenous administration of a fluorescence agent up to a current time is provided on the time line display portion 44. The elapsed time display line 49 is controlled so as to move to the right on the time line with time, as illustrated with FIG. 11.

In this case, fluorescence imaging is performed. Thus, imaging sequences for seven images are preliminarily set, as illustrated in FIG. 6. Because the number of imaging sequences is 7, seven sets of the image frame 45, the imaging condition field 46, the imaging timing line 47, and the permissible time display regions 48 are displayed.

Figure 11:
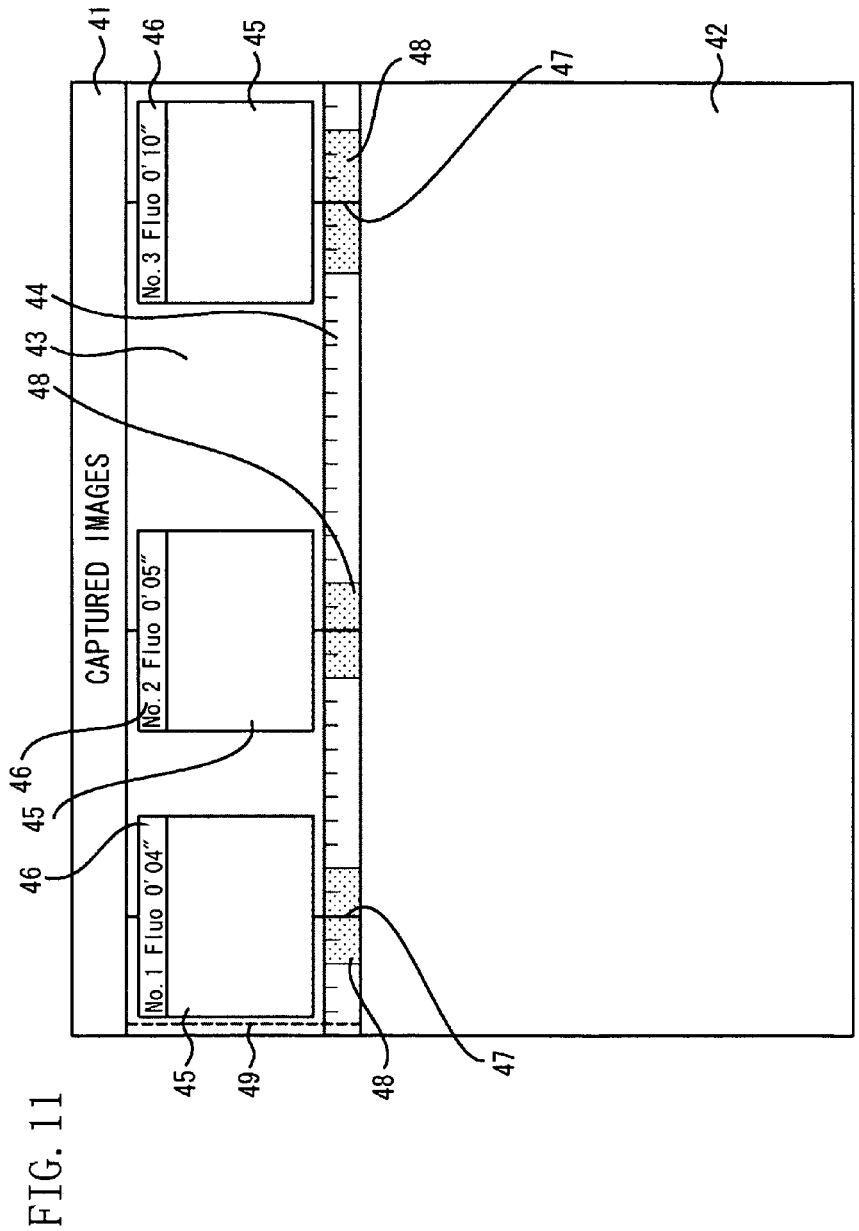
FIG. 11 illustrates an imaging screen before imaging is performed by fluorescence imaging.

When a display width of the thumbnail portion 43 is insufficient, as illustrated in FIG. 11, displaying of each thumbnail is performed within a range in which thumbnails can be displayed. In this case, all of the image frames 45, the imaging condition fields 46, the imaging timing lines 47, and the permission time display portions 48 can be displayed by laterally scrolling the thumbnail display portion 43.

Figure 12:
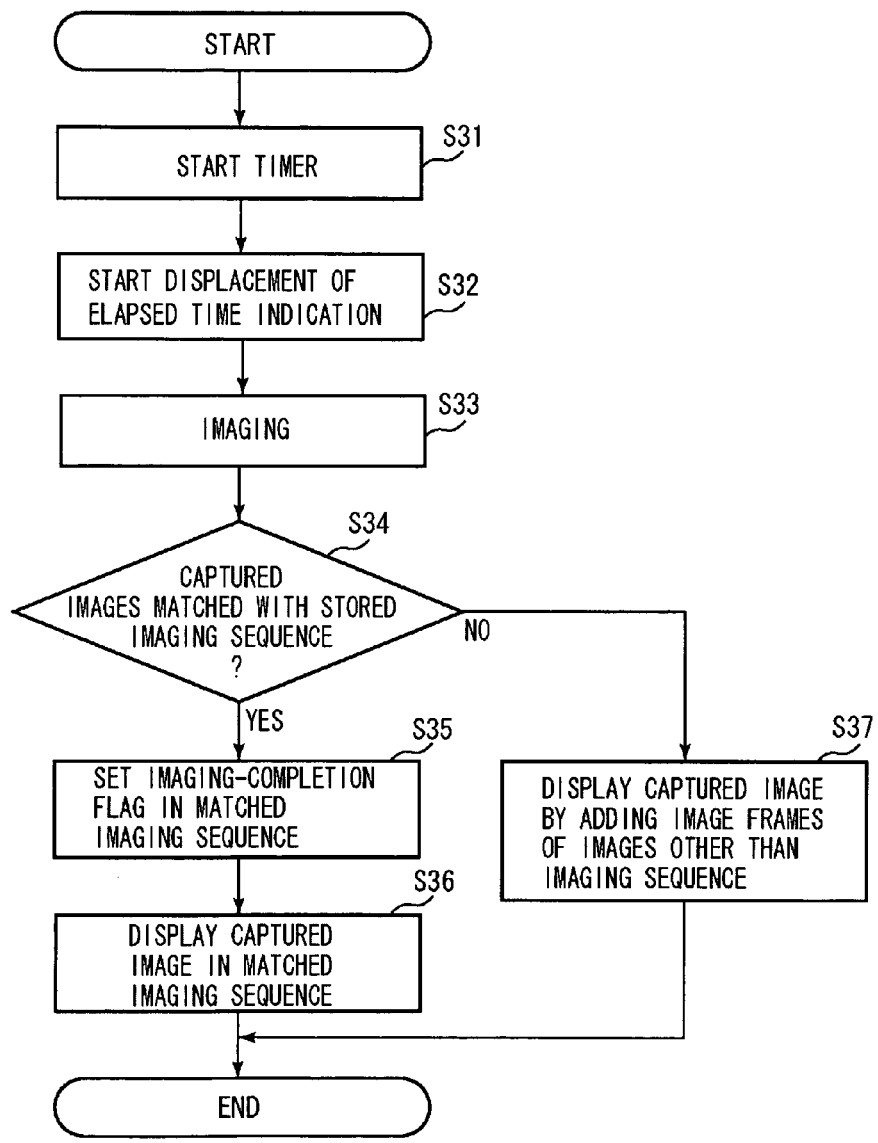
FIG. 12 is a flowchart illustrating an imaging operation performed in the fluorescence imaging mode.

FIG. 12 is a flowchart illustrating an imaging procedure of fluorescence imaging. An operator intravenously injects a fluorescence agent to a subject after the imaging screen 13 illustrated in FIG. 11 are displayed.

In step S31, the operator operates a timer start button of the examination instruction unit 12, simultaneously with the intravenous injection. The examination control unit 11 detects the operation performed on the timer start button. Then, in step S32, the timer unit 6 starts measurement of the elapsed time in response to the detection of the operation of the timer start button by the examination control unit 11. In addition, the display control unit 5 starts displacement of indication of the elapsed time display line 49.

In step S33, the operator makes the subject seated in front of the fundus camera 1. Then, positioning of the subject's eye and adjustment of the focus are performed. Imaging of the fundus of the subject's eye is performed by pushing an imaging switch (not illustrated) to cause a flash unit to emit light.

At that time, the operator pays particular attention to a positional relationship between the display position of the elapsed time display line 49 and the imaging timing line 47. Thus, the operator can recognize a current position on an imaging sequence. Consequently, the operator can easily grasp the next imaging timing.

The captured fundus image is stored as image data in the image storage unit 4 after photo-electrically converted by the digital camera 2. In addition, information representing an elapsed time and an imaging mode at the time of imaging the fundus image is stored in the image storage unit 4 together with the image data.

In step S34, when the imaging determination unit 8 detects that the image data is stored in the image storage unit 4, the imaging determination unit 8 performs a comparison of the image data with each imaging sequence stored in the imaging sequence storage unit 7. This comparison process is performed according to a flowchart illustrated in FIG. 14, which will be described below.

In step S34, if it is determined that the elapsed time is within the range of the permissible time, and that the imaging mode is matched with the imaging mode of imaging sequence (YES in step S34), the process proceeds to step S35, in which it is determined that the imaging according to the imaging sequence is performed. Then, an imaging-completion flag is set in the matched imaging sequence.

Figure 13:
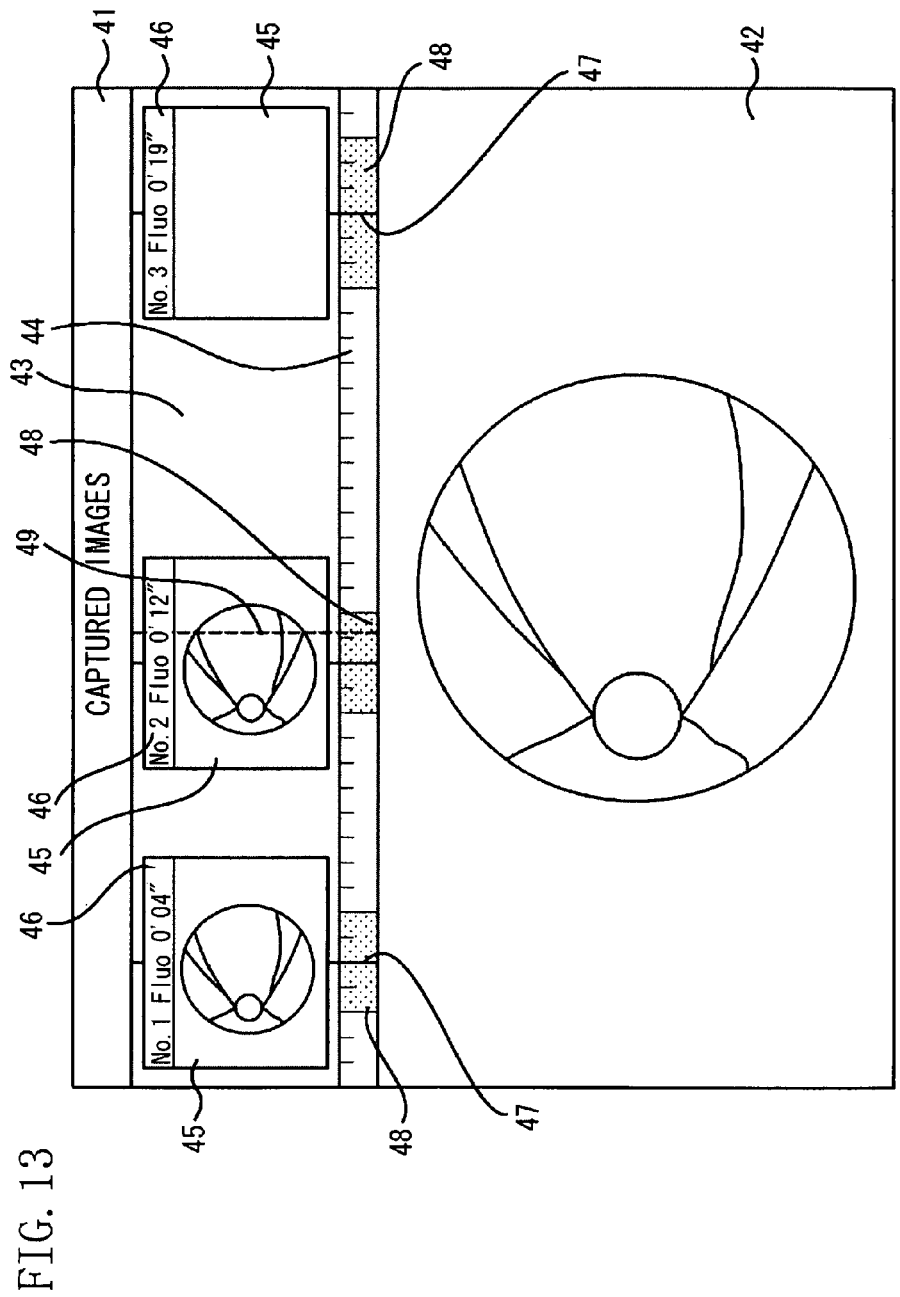
FIG. 13 illustrates an imaging screen after imaging is performed in the fluorescence imaging mode.

Subsequently, the process proceeds to step S36 in which the display control unit 5 displays a captured image in the main display region 42, as illustrated in FIG. 13. In addition, the captured image is displayed in the image frame 45 that meets the conditions.

An elapsed time when the imaging is actually performed is displayed in the imaging condition field 46 of the imaging sequence matched with the conditions. The operator recognizes the image frame 45, in which the captured image is embedded, and the imaging condition field 46. Thus, the operator can easily grasp that the sequence has been performed.

On the other hand, in step S34, if no imaging sequence matching the conditions with the captured image is found (NO in step S34), it is determined that imaging of an image captured according to the conditions other than those registered in the imaging sequences is performed. Then, the process proceeds to step S37 in which the display control unit 5 causes the display unit 13 to display the captured image in the main display region 42, and the display control unit 5 generates a new image frame in the thumbnail display portion 43 and displays the captured image in this image frame.

It is desirable that the newly generated image frame is displayed on the time line at the position corresponding to the elapsed time of the imaging of the image. However, if this image frame overlaps with the previous image frame or the next image frame, the newly generated image frame can be displayed at another position in the thumbnail display portion 43.

Figure 14:
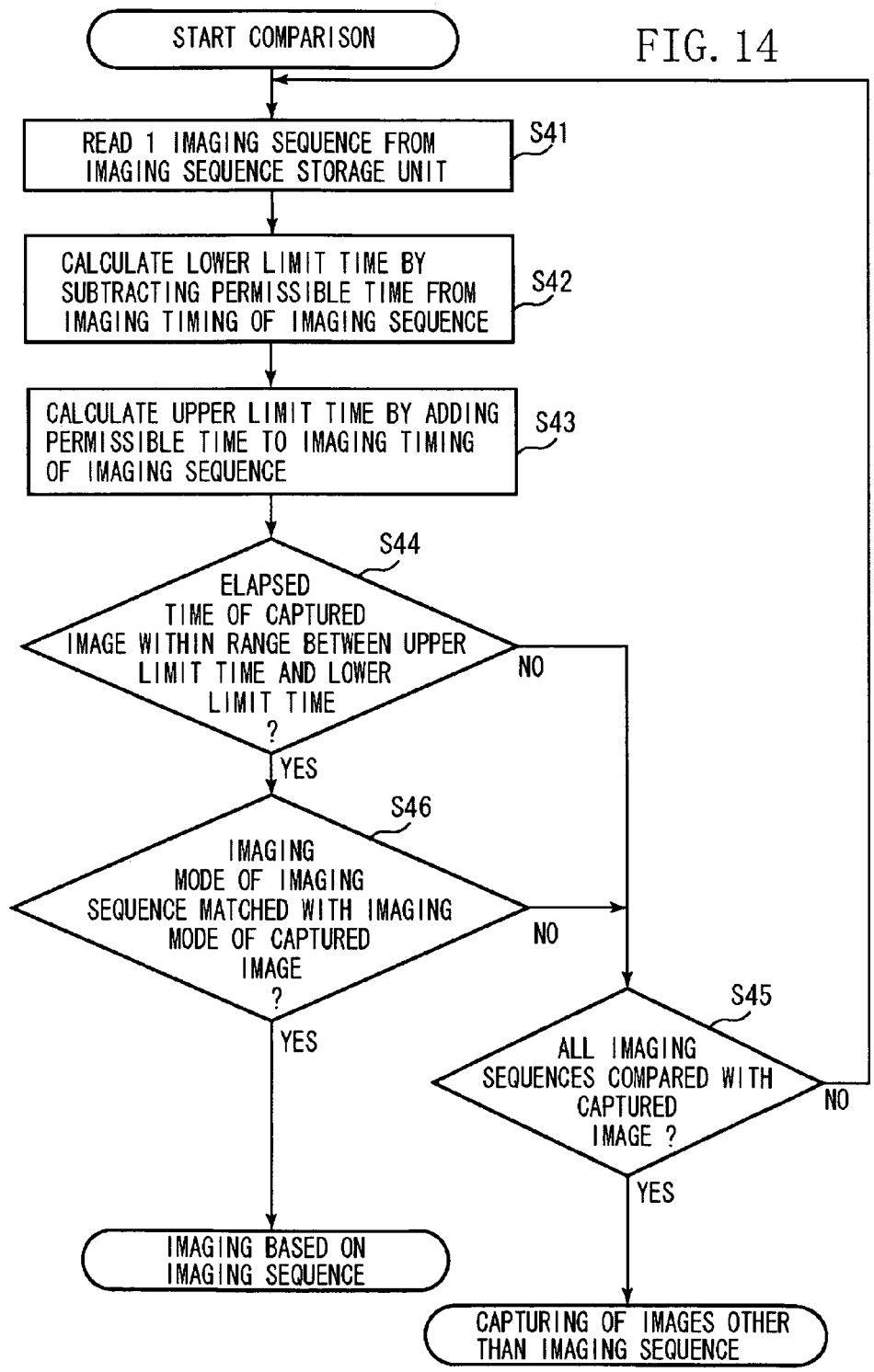
FIG. 14 is a flowchart illustrating a comparison process performed in the fluorescence imaging mode.

FIG. 14 is a flowchart illustrating the comparison process to be performed in step S34 illustrated in FIG. 12. First, in step S41, the first registered imaging sequence is read from the imaging sequence storage portion 7.

Next, in step S42, a lower limit time is calculated by subtracting the permissible time from the imaging timing registered in the imaging sequence. Then, in step S43, a value obtained by adding the permissible time to the imaging timing registered in the imaging sequence is calculated as an upper limit time.

Subsequently, in step S44, it is determined whether the time having elapsed since the intravenous administration of the fluorescence agent is within the range between the above-described lower limit time and upper limit time. If the elapsed time is not within the lower limit time and the upper limit time (NO in step S44), the process proceeds to step S45. In step S45, it is determined whether the comparison with all of the registered imaging sequences has been finished.

If it is determined that the comparison with all of the registered imaging sequences has been finished (YES in step S45), it is determined that imaging of an image captured according to the conditions other than those registered in the imaging sequences is performed. If it is determined that the imaging sequence is not the last one (NO in step S45), the process returns to step S41, because the next imaging sequence is present. Then, same steps are repeated.

In step S44, if it is determined that the elapsed time is within the range between the lower limit time and the upper limit time (YES in step S44), the process proceeds to step S46. In step S46, it is determined whether information of the imaging mode stored in the image storage unit 4 is matched with that of the imaging mode set in the imaging sequence. If the imaging modes are not matched (NO in step S46), the process proceeds to step S45. If the imaging modes are matched (YES in step S46), it is determined that the imaging is based on the conditions set in the imaging sequence.

According to the fundus image imaging apparatus of the present embodiment, the imaging sequences can easily be grasped by clearly specifying the imaging sequences. However, actually, sometimes, imaging is not performed according to the conditions set in the imaging sequence even when the imaging timing has passed. This is because the imaging cannot be performed at the designated imaging timing due to contingency such as a blink of subject or insufficient fixation thereof.

Figure 15:
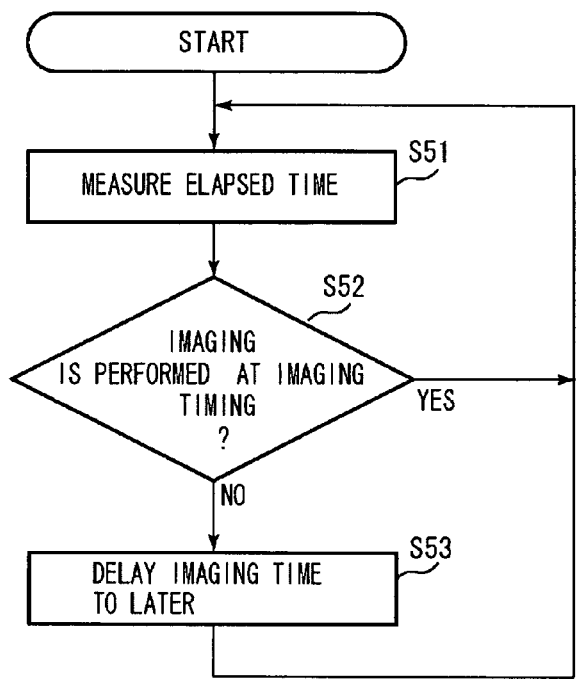
FIG. 15 is a flowchart illustrating an imaging sequence adjustment procedure.

In such a case, it is necessary to adjust the imaging sequences. FIG. 15 is a flow chart illustrating an adjustment procedure for adjusting the imaging sequences by the information processing unit 3. First, in step S51, the timer unit 6 starts to measure elapsed time since the start time designated by pushing a timer start button on the examination instruction unit 12.

Next, in step S52, the imaging sequence adjustment unit 9 compares the imaging timing registered in the imaging sequence with the elapsed time. If the imaging timing is less than the elapsed time and the imaging-completion flag is not set, the imaging sequence adjustment unit 9 determines that imaging is not performed even when the designated imaging timing has passed.

In step S52, if the imaging sequence adjustment unit 9 determines that imaging is not performed even when the imaging timing has passed (NO in step S52), the process proceeds to step S53. In step S53, the imaging sequence adjustment unit 9 calculates the imaging timing by adding a certain time to the elapsed time. On the other hand, in step S52, if the imaging sequence adjustment unit 9 determines that imaging is performed at the imaging timing (YES in step S52), then the process returns to step S51.

Next, the imaging timing, which is stored in the imaging sequence storage unit 7, at which imaging cannot actually be performed, is updated using the calculated imaging timing.

Figure 16:
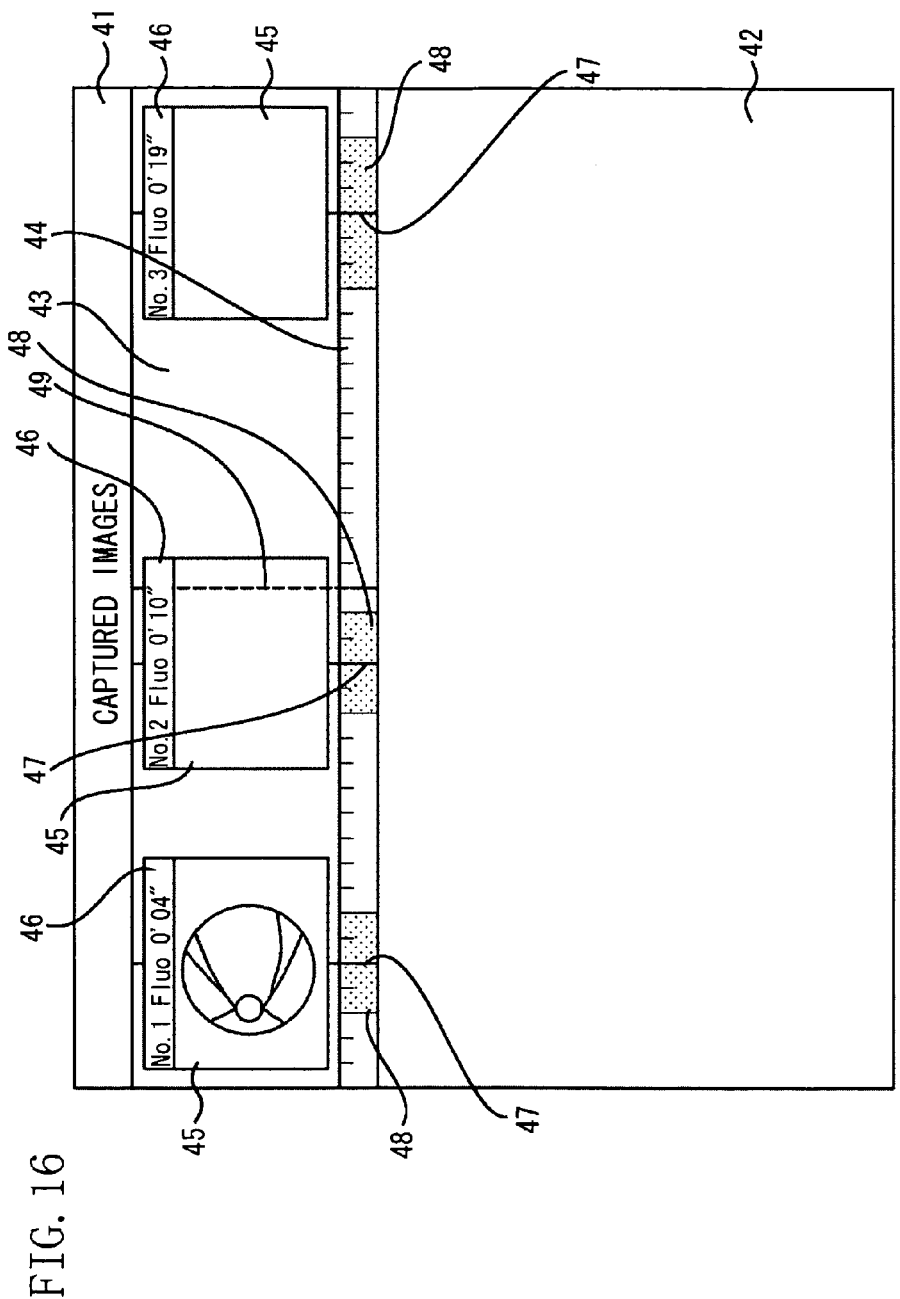
FIG. 16 illustrates an imaging screen before an imaging sequence is adjusted.

FIG. 16 illustrates the imaging screen when imaging is not performed even when the set imaging timing has passed. The elapsed time display line 49 has moved to the right beyond the imaging timing line 47 and the permission time display region 48. No image is displayed in the image frame 45 of the imaging sequence No. 2.

Figure 17:
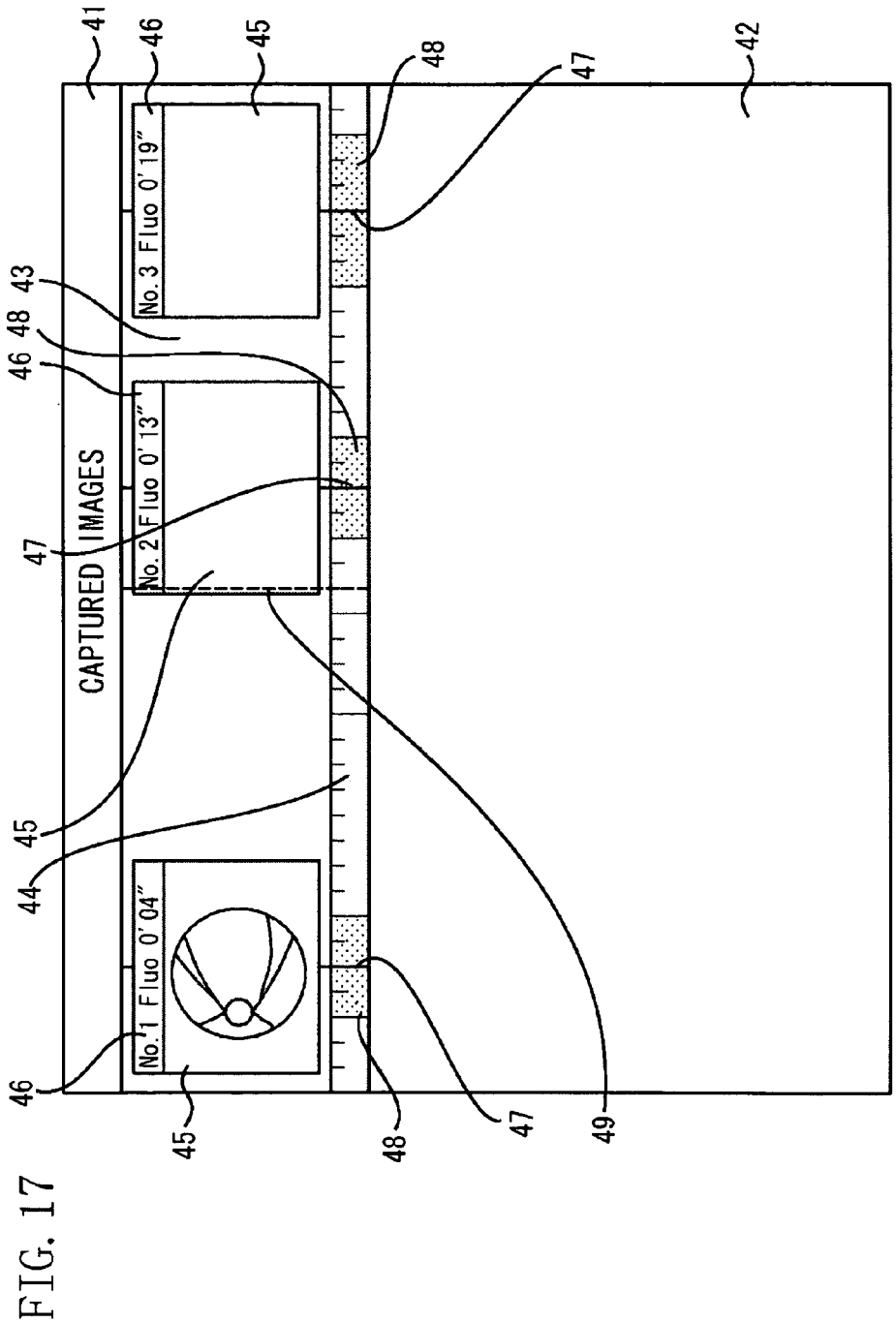
FIG. 17 illustrates an imaging screen after the imaging sequence is adjusted.

After the imaging timing is updated, the imaging timing line 47 and the image frame 45 are moved to the right, as illustrated in FIG. 17. On the imaging screen 41 in FIG. 17, the imaging timing, which is scheduled as 10 seconds since the intravenous administration of a fluorescence agent is performed, is shifted backward by 3 seconds. Thus, the scheduled time is updated to be 13 seconds.

Because the imaging timing is updated from 10 seconds to 13 seconds by the imaging sequence adjustment unit 9, the operator can try again to take a second image corresponding to the imaging sequence No. 2, which has not been captured.

When an examination is finished, since the imaging sequence is set according to a purpose of the examination, an appropriate diagnosis cannot be performed unless all of the set imaging sequences are finished.

Figure 18:
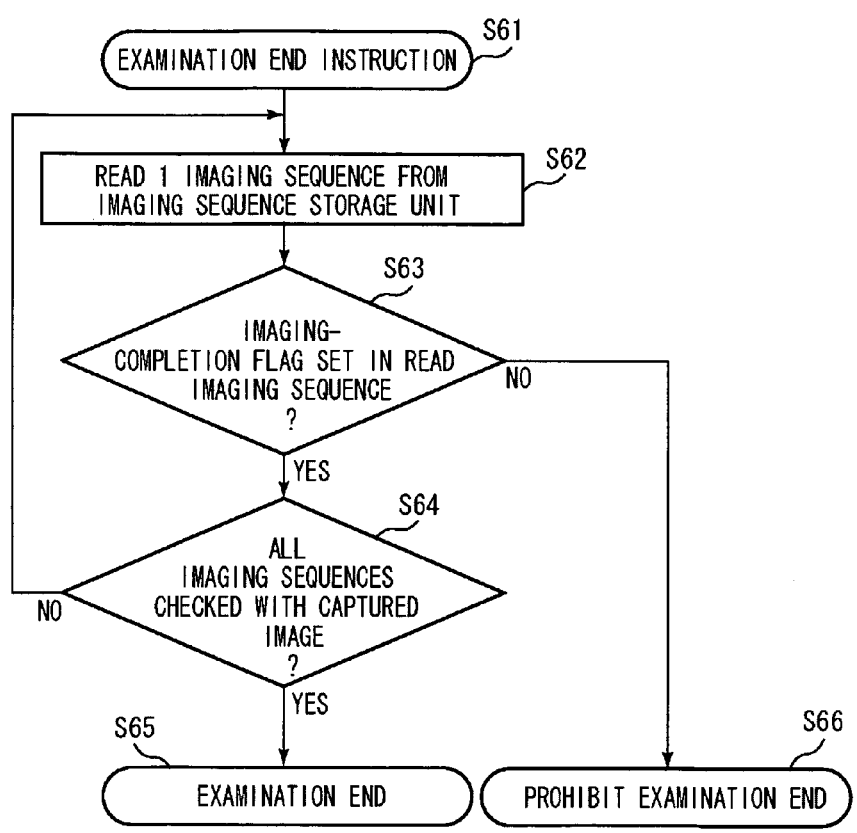
FIG. 18 is a flowchart illustrating an examination end determination operation.

FIG. 18 is a flowchart illustrating a process for determining whether the examination can be finished. First, in step S61, the examination control unit 11 detects an operation performed by an operator on the examination instruction unit 12.

Next, in step S62, the examination control unit 11 reads a leading imaging sequence from the imaging sequence storage unit 7. Subsequently, in step S63, the examination control unit 11 determines whether an imaging-completion flag for the read imaging sequence is set.

If the imaging-completion flag is set (YES in step S62), the process proceeds to step S64. In step S64, the examination control unit 11 determines whether checking of the imaging-completion flag has been completed on all imaging sequences. If the examination control unit 11 determines that the checking has not been completed (NO in step S64), the process returns to step S62. Then, the examination control unit 11 reads the next imaging sequence. Subsequently, the above-described checking process is repeated until the end of the imaging sequences is detected.

If the examination control unit 11 determines that the end of the imaging sequence is detected, and that the imaging-completion flag is set for all of the imaging sequences (YES in step S64), the process proceeds to step S65. In step S64, the fundus imaging apparatus according to the present embodiment is allowed to finish the examination. Thus, the imaging of the subjects is finished.

On the other hand, in step S63, if at least one of the imaging-completion flags is not set (NO in step S63), the process proceeds to step S66, and the apparatus is prohibited from finishing the examination.

If finishing of the examination is prohibited, the operator can continue to perform unfinished imaging sequences. At that time, the operator can check unfinished imaging sequences on the imaging screen illustrated in FIG. 9. Thus, the imaging of the rest of the imaging sequences can easily be performed.

Figure 19:
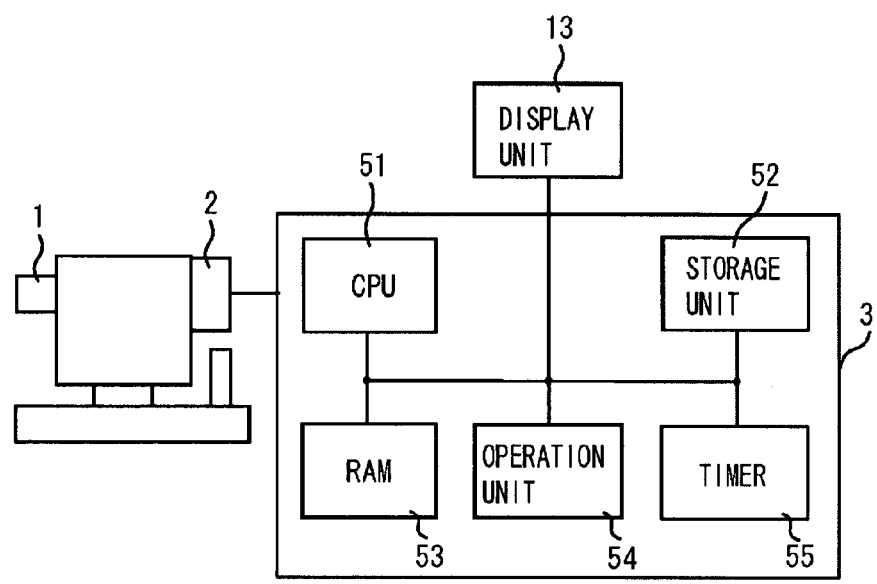
FIG. 19 schematically illustrates a configuration of hardware of an information processing apparatus.

FIG. 19 schematically illustrates a configuration of hardware of the information processing apparatus 3. A central processing unit (CPU) 51 is a control unit for controlling the entire information processing apparatus 3. The CPU 51 corresponds to the display control unit 5, the imaging determination unit 8, the imaging sequence registration unit 10, the imaging sequence adjustment unit 9, and the examination control unit 11, which are illustrated in FIG. 1.

A storage unit 52 is a storage apparatus, such as a hard disk drive, and stores programs that can be executed by a computer for integratedly controlling the entire information processing apparatus 3. The storage unit 52 stores also images captured by the digital camera 2, and the registered imaging sequences The storage unit 52 corresponds to the image storage unit 4, and the imaging sequence storage unit 7. A random access memory (RAM) 53 is a memory for temporarily storing programs and the like read from the storage unit 52.

An operation unit 54 includes a mouse, a keyboard, a touch panel, and the like and corresponds to the examination instruction unit 12. A timer 55 corresponds to the timer unit 6.

In the exemplary embodiment described above, an example of a fundus imaging apparatus is described. However, the present invention can be applied to a medical imaging apparatus, such as an X-ray imaging apparatus, for medical examinations.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-167061 filed Jun. 26, 2008, which is hereby incorporated by reference herein in its entirety.

What is claimed is:

1. A medical imaging apparatus comprising:
    an imaging unit configured to capture an image of a subject's eye;
    a registration unit configured to register an imaging sequence; and
    a display control unit configured to control a display unit to display a display configuration which indicates the registered imaging sequence,
    wherein, in a case where the image of the subject's eye has been captured not in accordance with the registered imaging sequence, the display control unit controls the display unit to display a new frame corresponding to a new imaging sequence.

2. The medical imaging apparatus according to claim 1, wherein the registration unit registers the imaging sequence including an imaging timing for capturing the image of the subject's eye,
    wherein the image of the subject's eye includes a fundus image of the subject's eye, and
    wherein the display control unit controls the display unit to display the display configuration which indicates the imaging timing and the fundus image of the subject's eye captured in accordance with the new imaging sequence in the new frame.

3. The medical imaging apparatus according to claim 2, further comprising a timer unit configured to measure elapsed time from a predetermined time,
    wherein the display control unit controls the display unit to display the display configuration which indicates the elapsed time on a time axis.

4. The medical imaging apparatus according to claim 3, wherein the elapsed time is a time having elapsed since an examination starts.

5. The medical imaging apparatus according to claim 2, wherein the registration unit registers the imaging sequence indicating a permissible time for the imaging timing according to age of the subject, and
    wherein the display control unit controls the display unit to display the display configuration which indicates the permissible time along a time axis.

6. The medical imaging apparatus according to claim 2, wherein the display control unit controls the display unit to display an image frame corresponding to the registered imaging timing, and
    wherein the display unit displays a fluorescence image of the fundus in the image frame.

7. The medical imaging apparatus according to claim 2, wherein the registration unit registers a permissible time for the fluorescence imaging timing, and
    wherein the display control unit controls the display unit to display the display configuration which indicates the permissible time along a time axis.

8. The medical imaging apparatus according to claim 7, further comprising an adjustment unit configured to adjust the imaging timing and the permissible time so as to delay the imaging timing and the permissible time by a predetermined time in a case where an imaging is not performed even when the imaging timing has passed.

9. The medical imaging apparatus according to claim 1, wherein the registration unit registers the imaging sequence including information indicating which one of right and left eyes of the subject is to be captured.

10. The medical imaging apparatus according to claim 1, further comprising: an imaging determination unit configured to determine whether an imaging-completion flag has been set in the imaging sequence; and
    an end prohibition unit configured to prohibit ending of an examination until the imaging determination unit determines that the imaging-completion flag has been set in the imaging sequence.

11. The medical imaging apparatus according to claim 10, wherein, when the examination includes more than one imaging sequence, the end prohibition unit prohibits ending the examination until the imaging determination unit determines that the imaging-completion flag has been set in all imaging sequences.

12. The medical imaging apparatus according to claim 1, wherein the registration unit resisters a plurality of fluorescence imaging timings for an image of a fundus of the subject's eye, and wherein the display control unit controls the display unit to display a display configuration which indicates the plurality of fluorescence imaging timings along a time axis.

13. The medical imaging apparatus according to claim 12, further comprising a determination unit configured to determine the plurality of fluorescence imaging timings according to an elapsed time of a fluorescence imaging of the fundus of the subject's eye.

14. The medical imaging apparatus according to claim 1, wherein the imaging sequence includes an imaging procedure comprising at least one of an imaging mode, information representing which of right or left of the subject's eye is to be captured, an imaging time, and a permissible time for imaging capture.

15. The medical imaging apparatus according to claim 1, wherein, in a case where the image of the subject's eye has been captured in accordance with the registered imaging sequence, the display control unit controls the display unit to display the captured image in a frame of the imaging sequence.

16. A medical imaging method comprising:
capturing an image of a subject's eye;
registering a imaging sequence; and
controlling a display unit to display a display configuration which indicates the registered imaging sequence and the captured image of the subject's eye,
wherein, in a case where the image of the subject's eye has been captured not in accordance with the registered imaging sequence, the controlling step controls the display unit to display a new frame corresponding to a new imaging sequence.

17. A non-transitory computer readable storage medium storing a computer-executable program of instructions for causing a computer to perform a method, the method comprising:
capturing an image of a subject's eye;
registering an imaging sequence; and
controlling a display unit to display a display configuration which indicates the registered imaging sequence and the captured image of the subject's eye,
wherein, in a case where the image of the subject's eye has been captured not in accordance with the registered imaging sequence, the controlling step controls the display unit to display a new frame corresponding to a new imaging sequence.

18. A medical imaging apparatus comprising:
an imaging unit configured to capture an image of a subject's eye;
a registration unit configured to register an imaging timing; and
a display control unit configured to control a display unit to display a display configuration which indicates the registered imaging timing,
wherein, in a case where the image of the subject's eye has been captured not in accordance with the registered imaging timing, the display control unit controls the display unit to display a new frame corresponding to a new imaging timing.

19. The medical imaging apparatus according to claim 18, wherein the display control unit controls the display unit to display the imaging timing along a time axis and the fundus image of the subject's eye captured at the new imaging timing in the new frame.

20. The medical imaging apparatus according to claim 18, further comprising a determination unit configured to determine a timing delayed from the registered imaging timing by a predetermined time as the new imaging timing.

\* \* \* \* \*